United States Patent
Trump et al.

(10) Patent No.: US 9,873,121 B2
(45) Date of Patent: Jan. 23, 2018

(54) REAGENT BOTTLE DOCKING SYSTEM

(71) Applicant: STRATEC Biomedical AG, Birkenfeld (DE)

(72) Inventors: Martin Trump, Pforzheim (DE); Thomas Lowien, Pfrozheim (DE); Matthias Barth, Karlsruhe (DE)

(73) Assignee: STRATEC Biomedical AG, Birkenfeld (DE)

( * ) Notice: Subject to any disclaimer, the term of this patent is extended or adjusted under 35 U.S.C. 154(b) by 116 days.

(21) Appl. No.: 15/095,337

(22) Filed: Apr. 11, 2016

(65) Prior Publication Data

US 2016/0296936 A1 Oct. 13, 2016

(30) Foreign Application Priority Data

Apr. 10, 2015 (LU) .......................... 92693

(51) Int. Cl.
*B01L 3/00* (2006.01)
*G01N 35/10* (2006.01)
*G01N 35/00* (2006.01)

(52) U.S. Cl.
CPC .......... *B01L 3/523* (2013.01); *G01N 35/1002* (2013.01); *B01L 3/5457* (2013.01); *B01L 2200/026* (2013.01); *B01L 2200/14* (2013.01); *B01L 2300/021* (2013.01); *B01L 2300/048* (2013.01); *B01L 2300/049* (2013.01); *B01L 2300/0627* (2013.01); *B01L 2300/0681* (2013.01); *G01N 2035/00851* (2013.01)

(58) Field of Classification Search
CPC ............................ B01L 3/523; G01N 35/1002
See application file for complete search history.

(56) References Cited

U.S. PATENT DOCUMENTS

| | | | |
|---|---|---|---|
| 5,665,315 A | 9/1997 | Robert et al. | |
| 2004/0170532 A1 | 9/2004 | Takahashi et al. | |
| 2009/0022631 A1 | 1/2009 | Ohashi et al. | |
| 2014/0242685 A1* | 8/2014 | Knoppke | B01L 3/502 435/289.1 |

* cited by examiner

*Primary Examiner* — Krishnan S Menon
*Assistant Examiner* — Dwan A Gerido
(74) *Attorney, Agent, or Firm* — 24IP Law Group; Timothy R DeWitt (57) ABSTRACT

A system for connecting a reagent container to a socket. The container has a cap with an outlet comprising a collar having an opening on its side, the collar surrounding a spout with a movable valve. The valve has a tube surrounded by a disk. A plug is centrally arranged within one end of the tube so the outer walls of the spout form-fit with the inner side of the tube and the inner walls of the spout form-fit with the outer side of the plug for closing the spout. The plug is connected to one end of the tube and a socket for accommodating the outlet of the container's cap. The socket comprises at least two movable levers to engage into openings of the collar and a socket gasket on one side for taking up the tube of the valve and tubing on the opposite side to drain liquids.

13 Claims, 13 Drawing Sheets

REAGENT BOTTLE DOCKING SYSTEM

CROSS-REFERENCE TO RELATED APPLICATIONS

The present application claims priority of Luxembourg Patent Application No. LU 92693 filed on Apr. 10, 2015. The aforementioned application is herby incorporated by reference in its entirety.

BACKGROUND OF THE INVENTION

Field of the Invention

The field of the invention relates to a system for reagent bottle docking.

Brief Description of the Related Art

Automatic analyzer systems in clinical diagnostics have to be supplied with different liquids to run biochemical processes and/or have to be loaded with operating fluids for integrated technical devices.

The liquids are usually provided in consumable bottles or containers to the analyzer systems, depending on their consumption, expiry or storability. The consumable bottles or containers must be loaded to various locations on the system, depending on the set-up of the respective analyzer system. The user has to replace them in due time to avoid, that they run empty. The empty bottles have to be disposed by the user.

The reagent containers have to be adapted to the specific needs of the reagents in terms of reagent expiry, storability or shelf life in warehouse. Further aspects that have to be taken into account for packaging of liquids are transportation as well as on board stability during use of the liquids in the analyser. The container must provide sufficient protection for the respective liquid from environmental influences like light, air, ambient gases and evaporation.

Typically analyzer systems need more than one type of reagents and therefore various liquids have to be stored and connected to the system. Very often there are at least two types of containers on a single analyzer system:

a. Containers that must be connected to tubings or couplings in order to provide the reagent "indirectly" via tubings to various modules in the analyzer system, and b. Containers that must provide their content "directly" to modules, i.e. modules that need to have access to reagents from above, like Pipettor modules.

It is important to have a clear and explicit user guiding in order to load the containers correctly due to the variety of reagent containers, loading procedures and their possible location on the system. If identical or similar containers must be loaded onto a system, the shapes of the containers or couplings will have to be different to prevent misconnection.

Nevertheless the user has to be very cautious when connecting containers and couplings. Even the use of different containers and couplings to prevent misconnection does not exclude the risk that the liquid paths can get in contact with each other, which resembles the worst case scenario that can lead to a complete contamination of the liquid system, parts of the analyzer system or the user himself.

Shelf life and on board stability of the reagents are very often compromised, because the container and its interface design focus more on the core functionalities of the liquid system and hardware interface of the container in order to reliably provide the liquid to the analyzer. For example, to empty air tight containers there are usually holes for pressure compensation where air/environmental gases or light can get in touch with the reagent. As a hole or cut-out is a simple and reasonable approach to the problem it is commonly accepted that reagent expiry is compromised. Pressure compensation with inert gases or other technical solutions would lead to higher analyzer and running costs, compromise design space and reliability of the analyzer.

The analyzer's liquid system has to be regularly checked and maintained. Therefore commonly cleaning fluids are used to rinse the tubings and components in the liquid paths. Usually the cleaning fluid is provided in one container to the system. The cleaning fluid coming from this container has to be switched over with a valve to the liquid paths that are to be cleaned. Or the cleaning fluid has to be provided in various containers or coupling adapters are necessary to connect to different liquid paths of the analyzer system.

A common requirement for process control in analyzer systems is that the presence of a loaded container needs to be detected. Additionally, more detailed information of the loaded reagent may be necessary for the system. This information is stored in bar codes or RFID-tags that are located on the containers. Often the user must read the information manually with a hand-held barcode scanner.

U.S. Pat. No. 5,665,315 A discloses an analyzer comprising a single box for the distribution of reagents and which is removable from, and connectable to, the said analyzer, the said box containing a plurality of flexible, retractable bags filled with reagent and a flexible bag for collecting the residues. The box is places on a horizontal supporting plate which slides along the side of the apparatus and which is mounted on springs. Upwardly orientated fixed metallic needles pass through orifices in the supporting plate In U.S. Patent Application Publication No. 2009/022631 A1 a sample container is described, that includes a cap that covers a container body holding a liquid sample containing a reagent and a test body. The cap includes an outer lid that covers the container body, an inner lid that is slidably attached to the outer lid and has an opening for dispensing the liquid sample, a shutter that has a shaft engaging with the inner lid, a translating unit that is fitted to the outer lid and translates sliding movements of the inner lid against the outer lid to rotation of the shutter around the shaft, and a pressing member that presses the shutter in a direction to close the shutter. The rotation of the shutter opens and closes a hole formed in the translating unit for dispensing the liquid sample.

U.S. Patent Application Publication No. 2004/0170532 A1 teaches a reagent vessel cap including a sealing member for sealing the opening of a vessel body; an pressurizing member linked to a retaining part for sealing the sealing member, for bringing the sealing member in close contact with the opening all the time, wherein when pressure is applied, the pressurizing member lifts the sealing member against the biasing force of itself to open the vessel and, when the pressure is eliminated, the pressurizing member returns to position by the biasing force to close the vessel by the sealing member; and a cap body capable of mounting the sealing member and the pressurizing member to the opening of the vessel body containing a reagent. The reagent is collected using the cap structure.

Various types of container with different shapes and/or couplings may be necessary to comply with the analyzer's architecture and differentiation to prevent misconnection, which may be based on:

Conflicts of the used container or bottle with the reagent distributor who ideally only wants to fill a single container type and size in order to run his filling line efficiently and to keep costs for logistics and stock keeping low.

Limitations on reagent shelf life and on board stability.

Pressure compensation has to be balanced against interaction of the reagent containers with surrounding gases: If certain reagents get in contact with air/environmental gases this may have a negative effect on reagent expiry and evaporation. In consequence sophisticated measures, i.e. pressure compensation with inert gases will have to be additionally installed on the system or the reagents will have to be replaced more often. This leads to additional user-interaction, higher system and running costs and may compromise assay performance and stability.

The reagents must be protected from light in a light surrounded area of the analyzer to extend lifetime while they have to be provided at the same time to modules that need a rather large cut-out in the reagent container to access the reagent. The same applies for couplings with transparent components or tubings that work like a light guide.

Limitations on user-friendliness:
  i. Risk of misconnection if identical couplings have to be used: Is very often the case for 'A-B' continuous loading concepts where at least two identical containers have to be connected to the system.
  ii. The user has to be familiar with various kinds of loading procedures in one system.
  iii. The user must be very cautious during reagent loading to prevent contamination of the liquid system due to wrongly connected containers and/or insufficient coupling interfaces that may prevent malconnection but do not fully prevent that the liquid interfaces can get in contact with each other and/or contaminate the user himself.
  iv. Manual identification procedures like scanning barcodes with hand-held devices leave a potential risk of manipulation and analyzer failures.

One container with liquid to clean/rinse each path of the system's liquid tubings cannot be directly used as a replacement for all reagent containers. This means that various containers with cleaning fluid and/or coupling adapters are necessary

SUMMARY OF THE INVENTION

It is an object of the invention to provide a system with reagent container enabling quick coupling to a docking station with a clear and explicit user interface The instant invention provides a system for connecting a reagent container to a socket comprising a reagent container for storing and providing liquids, wherein the container has a cap with an outlet comprising a collar having at least one opening on its side, the collar surrounding a spout with a movable valve; wherein the valve comprises a tube that is surrounded by a disk and a plug is centrally arranged within one end of the tube so that the outer walls of the spout form-fit with the inner side of the valve's tube and the inner walls of the spout form-fit with the outer side of the plug for closing the spout, wherein the plug is connected to the one end of the tube; and a socket for accommodating the outlet of the container's cap, wherein the socket comprises at least two movable lever to engage into the openings of the collar and a socket gasket for taking up the tube of the valve on one side and tubing on the opposite side to drain the liquids.

The movable levers of the socket can be spring loaded. It is intended that the disk of the valve can be centrally arranged in at least one conically-shaped connector tapering off starting at the tube of the valve.

The spout of the cap may comprise a filter.

The container can be a bottle with a rigid outer shell and a flexible inner bag, The outlet of the container and the socket of the docking station shall form-fit.

The cap may comprise a tag for storing information regarding the content or intended use of content of the container.

The tag can be a RFID label or a barcode.

The outer shell may have at least one opening for pressure compensation.

The outer shell and inner bag may be made of an opaque material.

The valve and collar may have means to limit maximal movement of the valve during opening.

The docking station may have a tongue suitable to engage in a corresponding groove of the cap to ensure insertion of correct container.

The at least two sockets may be arranged in a docking station.

Another object of the invention is a use of a system of any one of claims 1 to 13 for providing liquids to an automated analyzer system.

BRIEF DESCRIPTION OF THE FIGURES

The invention will now be described on the basis of figures. It will be understood that the embodiments and aspects of the invention described in the figures are only examples and do not limit the protective scope of the claims in any way. The invention is defined by the claims and their equivalents. It will be understood that features of one aspect or embodiment of the invention can be combined with a feature of a different aspect or aspects of other embodiments of the invention. It shows:

DETAILED DESCRIPTION OF THE INVENTION

The invention provides a docking station with an integrated ID concept to prevent loading/replacing of wrong containers and to prevent contamination of the liquid system and the user. The invention also relates to the provision of a liquid from a container in the docking station to other modules of the analyzer system, i.e. washer, measurement chamber or pipettor in order to reduce the variety of necessary container shapes or sizes and loading procedures.

The invention describes a reagent container with coupling interface/docking station, which can be used in automatic analyzer systems. It is an advantage of the disclosure of the instant invention that the supply of different types of reagents and operation liquids can be achieved by using only a single type of container without compromising requirements regarding reagent handling, reagent expiry, process control and user-friendliness.

The reagent distributor only has to fill one reagent container type and therefore time and costs to set-up the filling-line can be reduced to a minimum. This also has a positive effect on logistics and stock keeping on distributor and customer side.

The user only has to handle one reagent container type and for all reagents only one clear and explicit loading procedure must be followed. To prevent misconnection the coupling interface is mechanically keyed and it may hold barcode- or RFID-labels for identification. These labels will be automatically scanned for presence detection and process control after the container has been inserted into the docking station.

The coupling interface is designed in a way that the liquid lines do not get in contact when a bottle is being wrongly inserted into the docking station and therefore contamination of the liquid system with wrong reagents or liquids is prevented.

The reagent container is designed in a way that environmental influences like, air/environmental gases and light do not get in contact with the reagent inside and therefore reagent expiry isn't compromised. The air tight reagent container can be emptied without sophisticated and expensive measures for pressure compensation and it prevents negative influences on the reagent expiry due to evaporation or reactions with environmental gases.

The reagent container is a so-called "Bag in Bottle", "BIB" and consists of a rigid outer bottle and a thin and flexible inner bag that is filled with the reagent. The inner bag collapses when it is emptied. The outer bottle has at least one hole for pressure compensation to allow the inner bag to easily collapse. A pump or a similar device performs emptying actively. Throughout the whole emptying process the reagent does not get in contact with ambient air or ambient gases. Inner bag and outer bottle are coloured in black. Therefore, shelf life and on-board stability of light and/or air sensitive reagents are not compromised.

Apart from the actual "BIB" the reagent container is equipped with a separate "ID bottle cap" (see next page). This "ID bottle cap" combines the following functionality:

It provides the bottle closure and liquid coupling to connect the BIB to the docking station.

It provides installation space to integrate a filter or sieve element between bottle spout and liquid coupling. The filter does only get in contact with the liquid when the bottle closure opens. This avoids clogging of the filter due to getting partially in contact with liquid and drying again during transportation or handling.

It provides identification features:
mechanically keyed geometry to uniquely assign the ID cap to a reagent type;
the colour of the ID cap can be chosen in order to visually distinguish each individually keyed ID cap; and
a surface where a RFID label can be put onto to provide information to the system.

The mechanical keying of the cap and the docking station's interface are designed to prevent the liquid lines of reagent container and system to get in contact in case of a misconnection.

Furthermore, the liquid coupling of the cap is protected by an integrated collar to
protect the liquid coupling from accidental opening or closing; and
avoid contamination of the user during bottle handling during loading/unloading.

During storage and transport, the reagent container's orientation is with the liquid coupling up. This reduces the risk of leakages that may occur due to defective bottle closures or accidently opened closures due to vibrations or shocks to a minimum.

To protect the liquid interface from dust and dirt during storage and transport it must be covered by a protective cap or lid. Ideally this lid can be designed in a way to additionally prevent the bottle closure from accidental opening due to vibrations or shocks during transport. Before inserting the reagent container into the docking station the user must remove this protective lid. The bottle closure remains in closed condition. It is opened 'automatically' by mechanism when the user inserts the bottle into the docking station.

To load the reagent container into the docking station the user grabs the reagent container at its bottle and inserts it upside-down into the docking station. The user does not get in contact or even near the liquid coupling because connection of the liquid lines is performed inside the docking station 'automatically'. Therefore the risk of contamination of the user and the analyzer's liquid system is reduced to a minimum.

Another positive effect of inserting the reagent container upside-down into the docking station is that it significantly reduces the effort to empty the bottle. A suction lance or similar devices are not necessary as the liquid content of the BIB drains to the spout by gravity. This reduces residues and dead-volume to a minimum.

The docking station is designed to provide a certain amount of liquid depending on the analyzer system and mechanical interfaces to load various numbers of reagent BIBs. As mentioned before, the interfaces are mechanically keyed to prevent misconnecting the liquid lines and therefore preventing contamination of the liquid system with wrongly loaded reagents.

The liquid lines can only get in contact after the mechanical key features of reagent container and docking station match correctly. It is only possible to fully insert the reagent container into the docking station if the parts of the coupling fit. The liquid coupling is designed in a way to provide a liquid and air-tight connection. The docking station mechanism is designed in a way that it can be easily taken out of the analyzer by the user for cleaning purposes. Therefore, electronic components for RFID reading or bottle presence detection are attached as separate parts.

The bottle closure opens after the liquid interface of bottle and gasket of the docking station got in contact. The user must fully insert the bottle into the gasket until the fully open position is haptic and acoustically indicated by a spring-loaded bistable mechanism (comprising levers and two springs). This mechanism is used to open and close the bottle closure and to keep it in a correct position inside the gasket of the docking station. It therefore ensures a gas and liquid tight coupling. The bottle itself is basically kept in position by gravity.

The user removes the reagent container out of the docking station by pulling the bottle upwards out of the docking station. During the upward movement of the bottle the closure is being closed automatically by the spring-loaded bistable mechanism. The closure remains in the gasket until the bottle is closed. The closed position of the closure is indicated acoustically and haptic by the spring loaded bistable mechanism.

To prevent leakages and liquid flowing back into the bottle the analyser system must ensure that no liquid can flow back through the coupling e.g. by the use of a check valve or peristaltic pump.

An RFID-label that is for instance located on the ID-cap is automatically scanned after the bottle has been inserted. The RFID tag may keep information about the loaded reagent, which is provided to the analyzer system for process control. RFID reading is also used for the presence detection of the bottle.

The System also calculates the remaining amount of liquid by counting the number of tests and writes the result back to the RFID tag.

The docking station is equipped with sensors to check if the liquid lines are properly connected and if reagent bottles run empty. These sensors are located close to the docking station and optically check the liquid lines for air bubbles that indicate a leakage. The tubing or coupling parts must be made of transparent material to allow proper and reliable detection, where the liquid sensors are located.

It is also necessary to check the temperature of the liquid coming from the bottles, so the temperature can be adjusted to lie within a specified range. Thus, a temperature sensor has to be located close to the coupling of the docking station. The information of the sensors is provided to the analyzer system for process control.

The docking station may have a panel that uniquely labels each loading interface with information like text or numbers. The panel may further have at least one LED. Such a LED visually indicate the status of the docking station and may indicate which reagent containers have to be loaded or removed by the user.

All liquid paths of the docking station can be cleaned and rinsed by replacing the reagent container with a container filled with a cleaning fluid. Depending on the purpose and cleaning procedure there may be more than one kind of cleaning fluids needed. Thus, various cleaning fluids may be provided. The ID Cap of the containers can be designed as 'master keys' that mechanically match every port of the docking station.

Reagents from the docking station are provided via tubing connections to other modules of the analyzer system. Especially for pipettor modules that must have access to the liquids from above the reagents of the docking station can be provided to reservoirs located on the deck of the analyzer. The filling level of the reservoirs is detected for process control by the liquid level detection (LLD). The reservoirs shall be designed in a way that negative influences from ambient light or air are on the quality of the liquid are reduced to a minimum, e.g. by a black or opaque shell with an opening for pipettor access that is as small as possible in order not to compromise on-board stability of the provided reagent. The user can easily take the reservoirs out of the analyzer for cleaning purpose.

The advantages of the invention of the present disclosure can be summarized as follows:

a. The solution offers a very clear and explicit user interface for the exchange of consumable liquids. Thus, less user operations, minimized maintenance due to less or no cleaning effort result.
b. The docking station design and its technical features avoid possible mix-up or confusion in terms of differentiating between bottles and containers that are in use and the ones that need to be exchanged.
c. The container and coupling concept reduces the risk of contamination of the system and user to a minimum. The risk for the user to get in contact with the reagents is low.
d. Small dead volumes due to upside-down arrangement of the bottles result in less waste of unused reagents, less packaging costs, less loading operations by the user.
e. Improved storability, shelf life and on-board security, because of light and air-tight container even when installed on the analyzer.
f. Highly light and/or air sensitive reagents can be used, because the container material can be adapted to the chemical needs.
g. The coupling at the container can be equipped with additional features like filter elements. The filter is placed in or part of the bottle closure. It is located in a way that it does not get in contact with the liquid before the closure opens to avoid clogging.
h. Reduction or even elimination of evaporation to improve assay performance and stability.
i. The docking system reduces space constraints in a system layout as it allows implementing fewer components and flexibly locating some of the still necessary components in areas that do not need to be accessed by a user.
j. The docking system has a big potential to reduce effort in hardware and software to realize a loading concept for cleaning fluids to each liquid path of an analyzer system compared to commonly used approaches, like a lower technical complexity and improved overall reliability, less maintenance, less system size and costs.
k. The reagent distributor can run his filling-line and logistics with high efficiency because only one bottle and coupling interface type needs to be handled and taken care of. From a manufacturer or distributor perspective it generates benefits in marketing and customer satisfaction. From a consumer or user perspective this reduces costs.

Figures 1A, 1B:
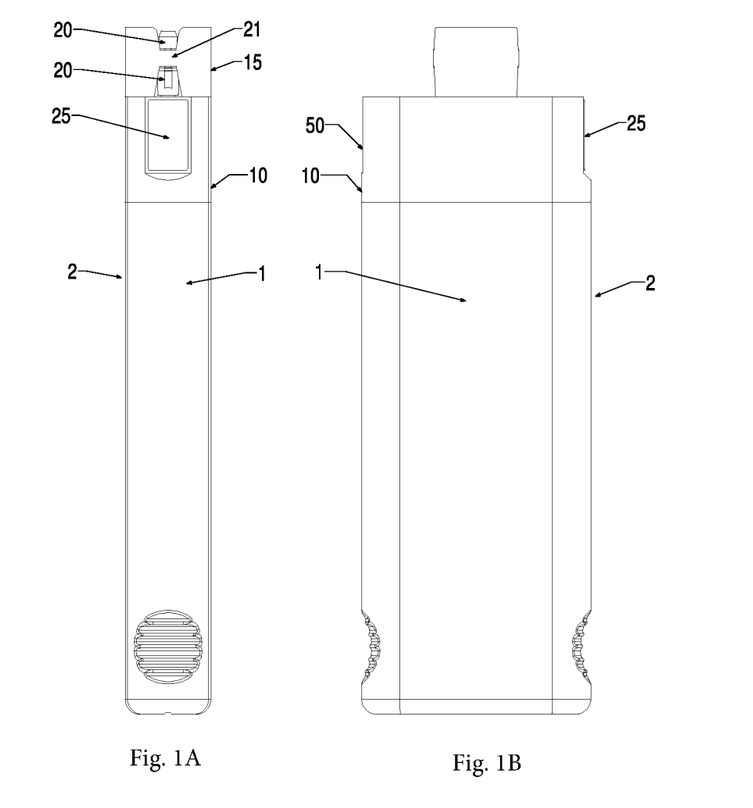
FIGS. 1A-1C are schematic overviews of a container in a side view (FIG. 1A), front view (FIG. 1B) and top view (FIG. 1C).
Figure 1C:
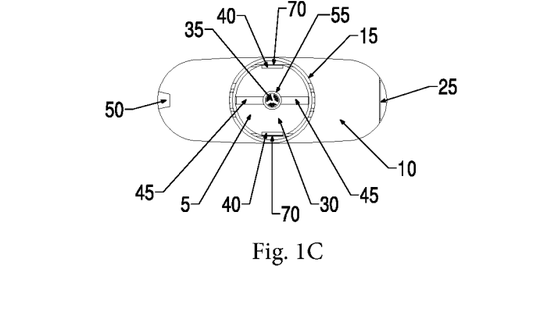

FIGS. 1A-1C show schematic overviews of a container 2 from side, front, and top views, respectively. The container 2 comprises cap 10 and rigid outer shell 1. The cap 10 may have a label, like a RFID tag 25 on one side. On top of the cap is the opening arranged, which comprises a collar 15 having two openings 20 on opposite sides, wherein an opening 20 on one side is divided by a division bar 21. A groove 50 may be arranged on the side opposite to the side having the RFID tag 25. The groove 50 form fits in corresponding tongues arranged within the socket 110 (not shown in this figure).

FIG. 1C shows that the valve 5 is arranged within collar 15. On top of the valve's tube is a filter 35 arranged. The disk 30 surrounds the tube. Connectors 45 are connected to the centrally arranged tube 55 and are arranged perpendicular to the disk 30. The disk 30 has on opposite sides' valve stops 40 ensuring that the valve is not able to pass collar valve stops 70. Thus, the valve cannot slip-out of collar 15. Cap 10, groove 50 and RFID tag 25 are also shown in the bottom part of FIG. 1.

Figure 2A:
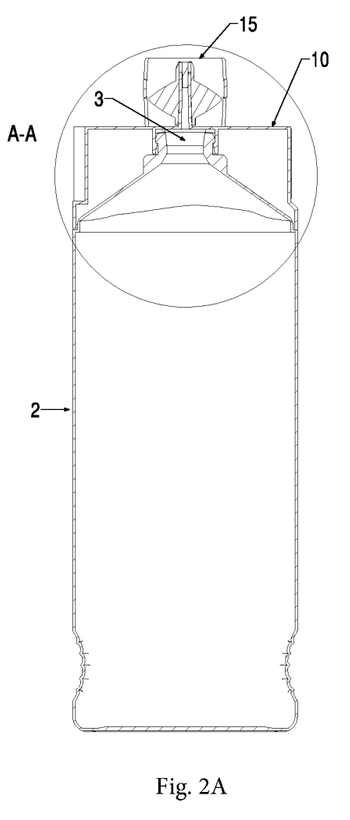
FIGS. 2A-2B are schematic overviews of a sectional drawing through axis A-A as indicated in FIGS. 1A-1C (FIG. 2A), detail enlargement as indicated circle B (FIG. 2B).
Figure 2B:
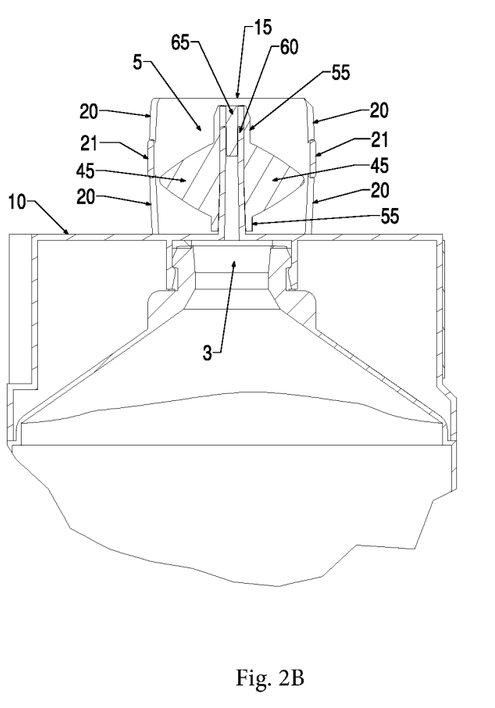

FIG. 2A shows sectional drawings of container 2 and cap 10 through axis A-A as indicated in FIG. 1A (left), and a detail enlargement of the sectional drawing as indicated in circle B in FIG. 2B. The cap 10 is arranged above opening 3 of the container 2. The collar 15 surrounds valve 5, which surrounds with its tube 55 spout 60. Division bars 21 divide each opening 20 on opposite sides of the collar 15. Plug 65 is arranged within the end of spout 60. Thus, spout 60 is closed. The section goes through connectors 45 showing their conical shape tapering off from tube 55.

Figure 3:
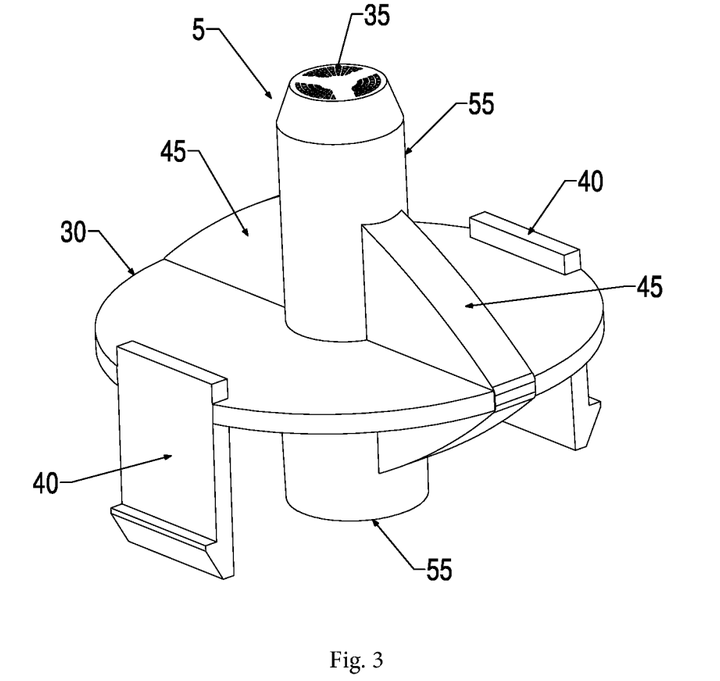
FIG. 3 is a perspective drawing of a valve.

FIG. 3 shows a perspective drawing of valve 5. Again, the conical shape of connectors 45 on both sides of tube 55 can be seen. The disk 30 is centrally and perpendicular arranged to the connector 45. A valve stop 40 limits maximal movement of the valve during opening in collar 15, because valve stop 40 cannot pass collar valve stop 70 (not shown in this figure) and thus ensures that the valve 5 cannot slip out of collar 15 (not shown in this figure). On top of tube 55 is a filter 35 arranged.

Figure 4:
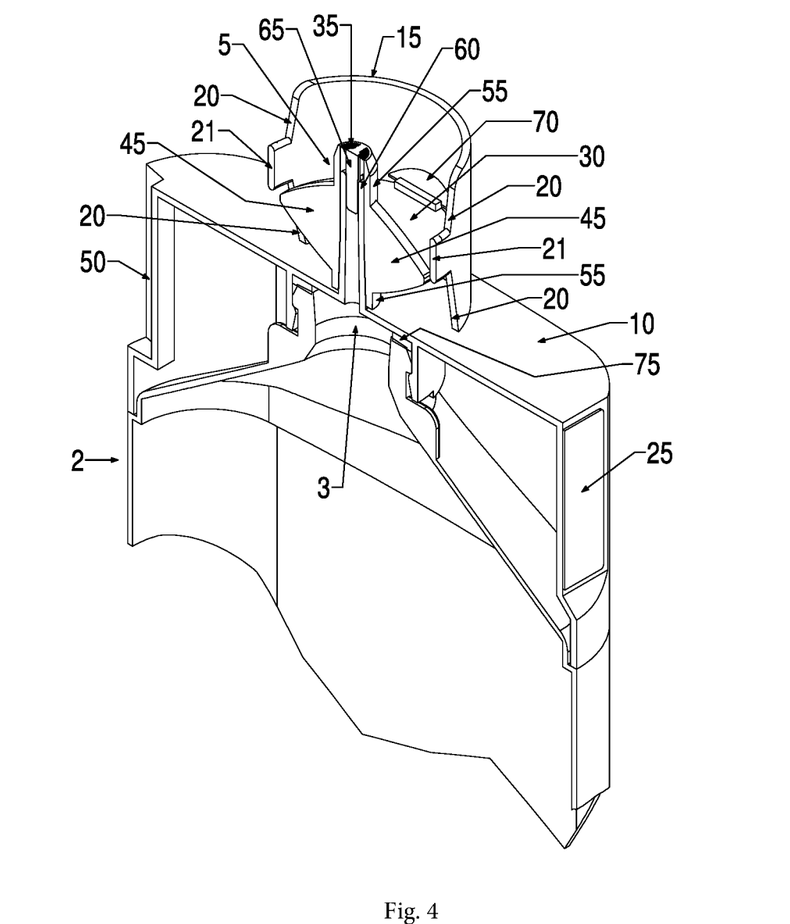
FIG. 4 is a sectional drawing of a container with cap and valve.
Figure 5:
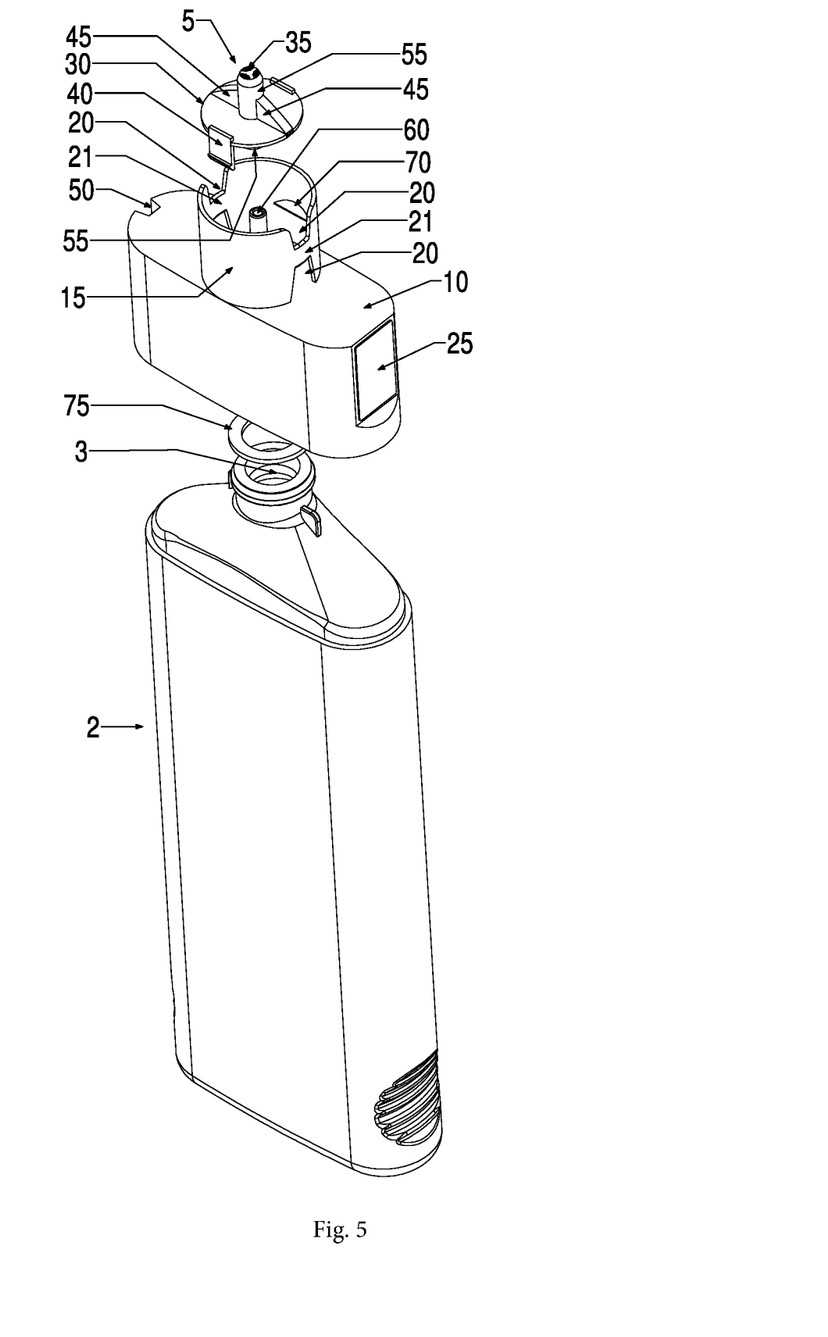
FIG. 5 is an exploded view of the valve shown in FIG. 4.

FIG. 4 shows a sectional drawing of a container 2 with cap 10 and valve 5. FIG. 5 shows an exploded view of the FIG. 4. Cap 10 is arranged onto the opening 3 of container 2. A gasket 75 is arranged between cap 10 and opening 3 of container 2. Cap 10 has on one side a RFID tag 25 and on the opposite site a groove 50 for engaging with a tongue of the socket (not shown).

It can be well seen that division bars 21 divide the openings 20 on both sides of collar 15. Collar valve stop 70 prevents a slip-out of valve 5 out of collar 15, when the bottom part 41 of valve stop 40 comes into contact with collar valve stop 70.

Valve 5 comprises a tube 55 surrounding spout 60. Tube 55 is surrounded by disk 30. Perpendicular to the disk are connectors 45 arranged on opposite sides of tube 55. The end of spout 60 can be closed by plug 65 that is connected to tube 55 of the valve and arranged within the opening of spout 60. The connection of plug 65 with tube 55 of the valve may further comprise a filter 35, which can be formed as a sieve.

Figure 6A:
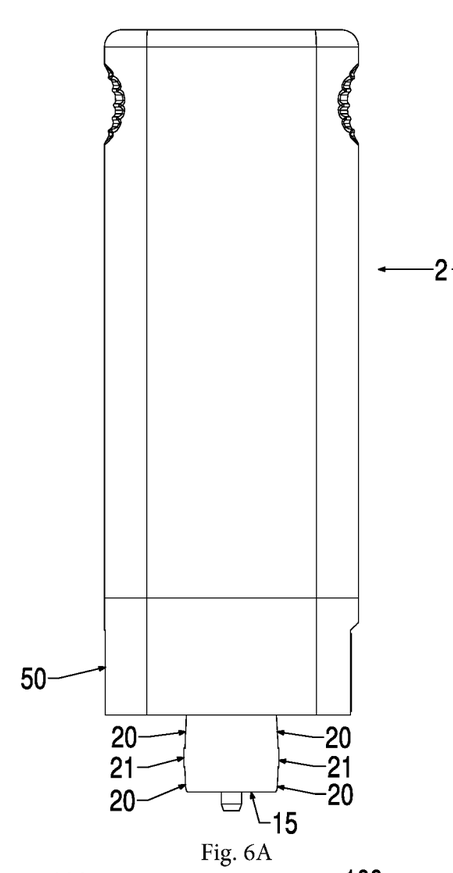
FIG. 6A is a front view of a container and socket.
Figure 6B:
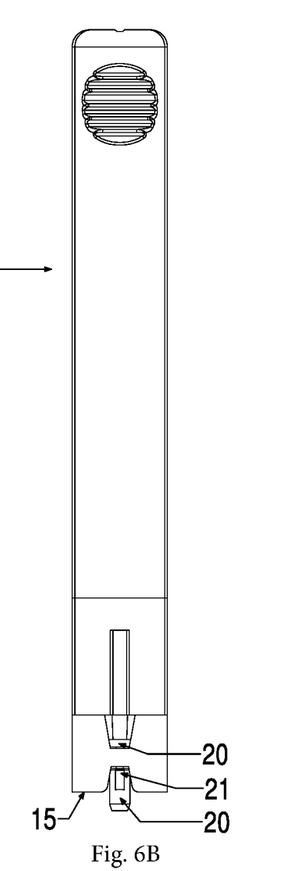
FIG. 6B is a side view of container and socket.
Figure 6C:
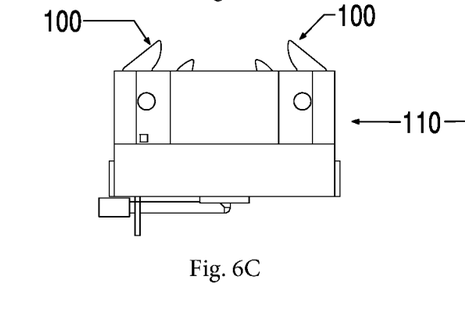
FIG. 6C is a front view of a disassembled portion of the container and socket shown in FIG. 6A.
Figure 6D:
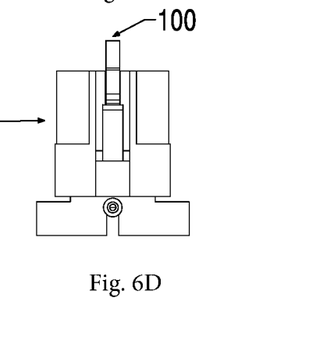
FIG. 6D is a side view of a portion of the container and socket shown in FIG. 6B.

FIGS. 6A and 6C show a front view and FIGS. 6B and 6D shows a right side view container 2 and socket 110. The opening of the container (not shown) that is surrounded by collar 15 is closed. Levers 100 of socket 110 can be seen.

Collar 15 has openings 20 being divided by division bar 21. Groove 50 on the side of cap 10 shall engage with a corresponding tongue (not shown) of socket 110.

Figure 7A:
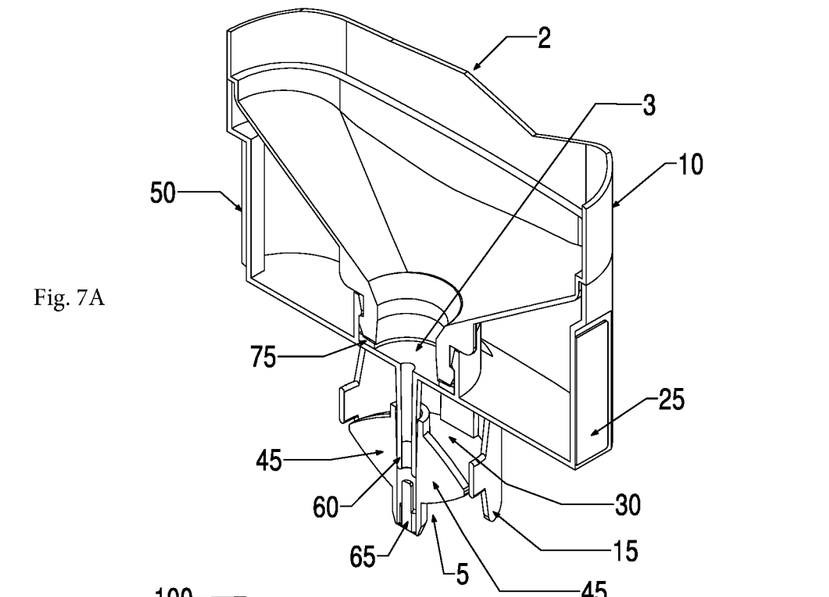
FIGS. 7A and 7B are sectional views on the cap of the container and the socket.
Figure 7B:
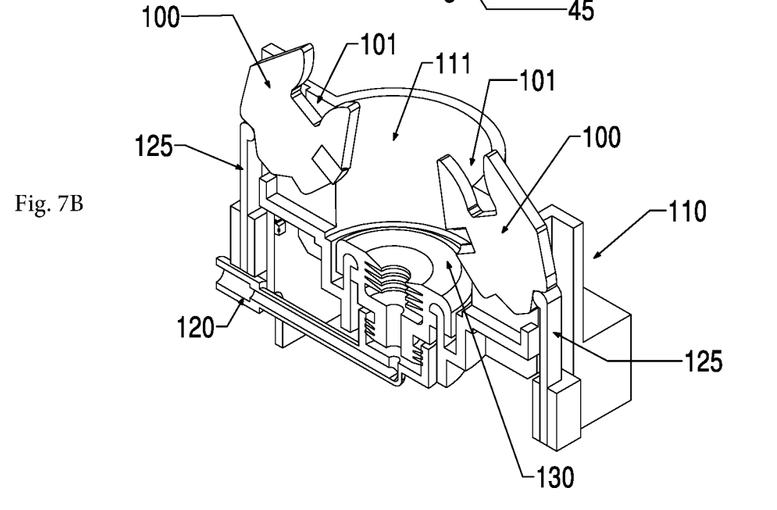

FIGS. 7A and 7B show a sectional view of cap 10 arranged above opening 3 of the container 2. Between opening 3 of the container and cap 10 is a gasket 75 to prevent leakage of the liquid. The socket 110 has a opening 111, which can take up the collar 15 surrounding valve 5. Again, tube 55 surrounding spout 60, plug 65, disk 30 and connector 45 of the valve can be seen. A RFID tag 25 is arranged on the opposite side of cap 10 having groove 50.

The levers 100 of socket 110 are spring 125 loaded, so that the opening 101 of the lever 100 are directed towards collar 15 and valve 5 of the container 2. On the bottom of opening 111 of socket 110 is socket gasket 130 arranged. Socket gasket 130 accommodates tube 55 of valve 5 and prevents leakage of liquid when the valve 5 is opened because plug 65 does no longer close spout 60. On the opposite side of socket gasket 130 for accommodating tube 55 is tubing 120 arranged for draining liquid and provide transport of the liquid to an automated analyzer system (not shown).

Figure 8A:
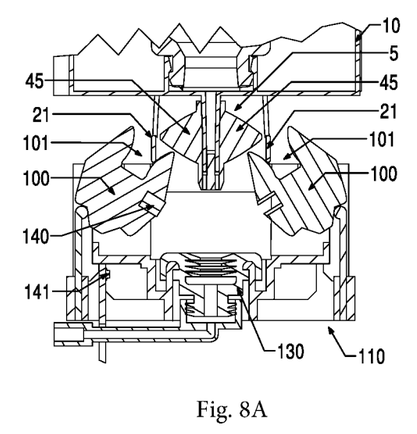
FIGS. 8A-8D show a sequence of sectional views of a cap connecting to the socket.

FIGS. 8A-8D show a sequence of sectional view of a cap 10 connecting to socket 110. The cap 10 can only enter socket 110 if the key 50 matches to its counterpart (not shown) in socket 110. In FIG. 8A it can be seen that the division bars 21 get in contact with the inner part of the lever 100, because opening 101 of the lever 100 is directed towards them.

Figure 8B:
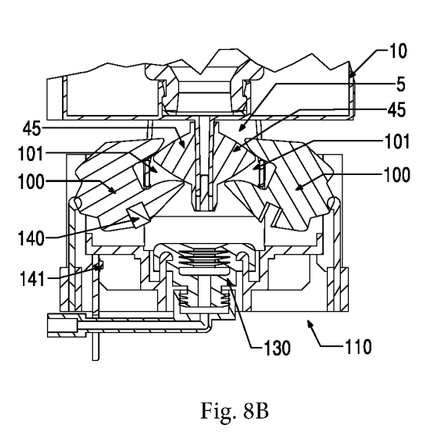

FIG. 8B shows that the conically-shaped connector 45 engage also into the opening 101 of lever 100, so that the lever rotate downwards. Thus, both levers 100 clutch valve 5 via connectors 45.

Figure 8C:
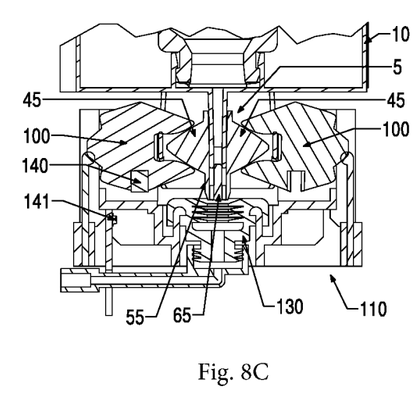

FIG. 8C shows that valve 5 will be additionally moved downwards, when the container is further moved into socket 110. Although the tip of valve 5 has already entered socket gasket 130, valve 5 is still closed, because plug 65 is arranged within the tip of tube 55 of valve 5. The connectors 45 are clutched in-between the arms of both levers 100.

Figure 8D:
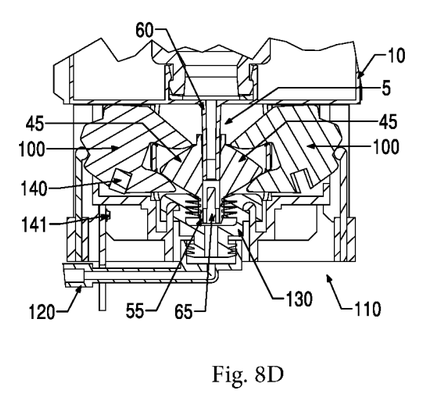

FIG. 8D shows that the valve 5 is still moved downwards by the arms of levers 100 clutching connectors 45. This movement takes place in addition to the downwards-projected movement of cap 10 into socket 110. The tip of valve 5 is well surrounded by socket gasket 130, so that plug 65 has left tube 55 of valve 5, thus opening spout 60. Liquid leakage is prevented, because opening of spout 60 occurs not before the tip of tube 55 is well surrounded by socket gasket 130. After opening spout 60 a liquid connection between the content of the container and tubing 120 is established, so that the liquid can be drained for further processing to the automated analyzer system.

It has to be noted that the embodiment shown in FIGS. 8A-8D further comprises a sensor 141 (hall sensor) for detecting a change in the position of magnet 140. It is obvious for a person skilled in the art that other types of sensors may be suitable to detect movement of levers 100.

Figure 9:
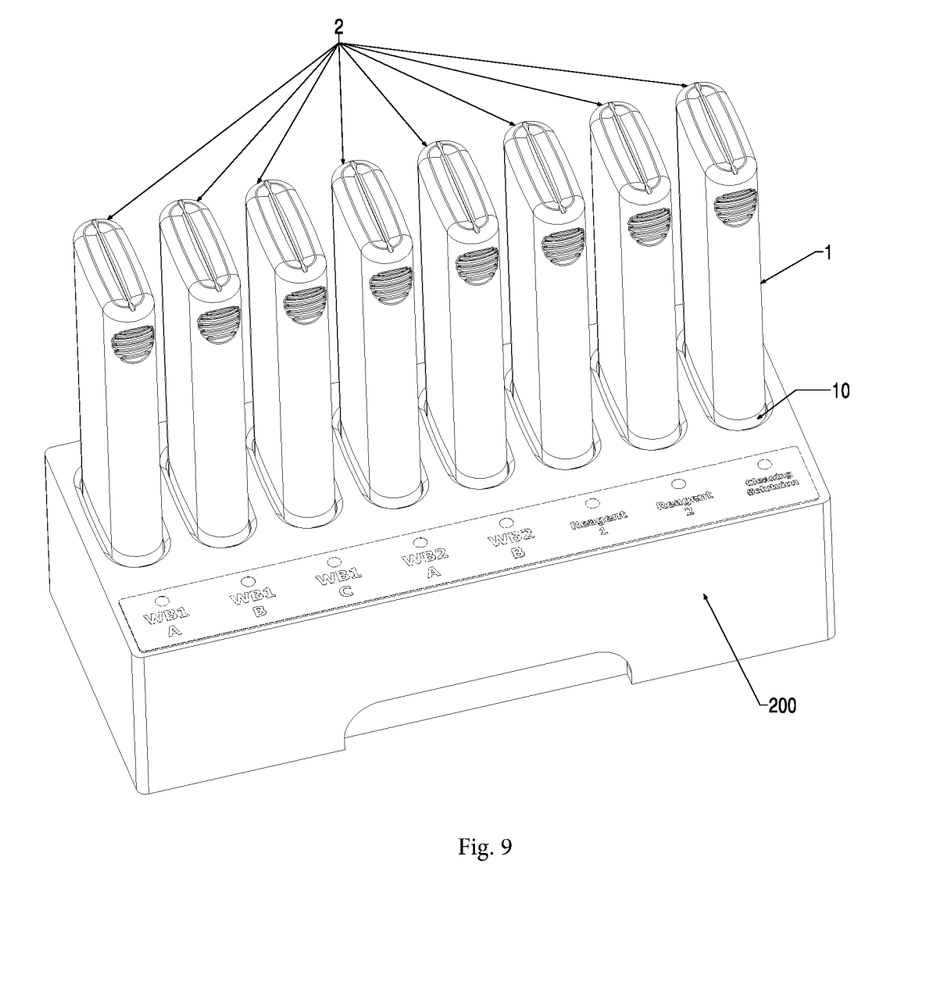
FIG. 9 is a perspective view of a docking station.

FIG. 9 shows a schematic overview of a docking station 200 with multiple containers 2 with a rigid outer shell 1 and cap 10 are inserted top-down.

Figure 10:
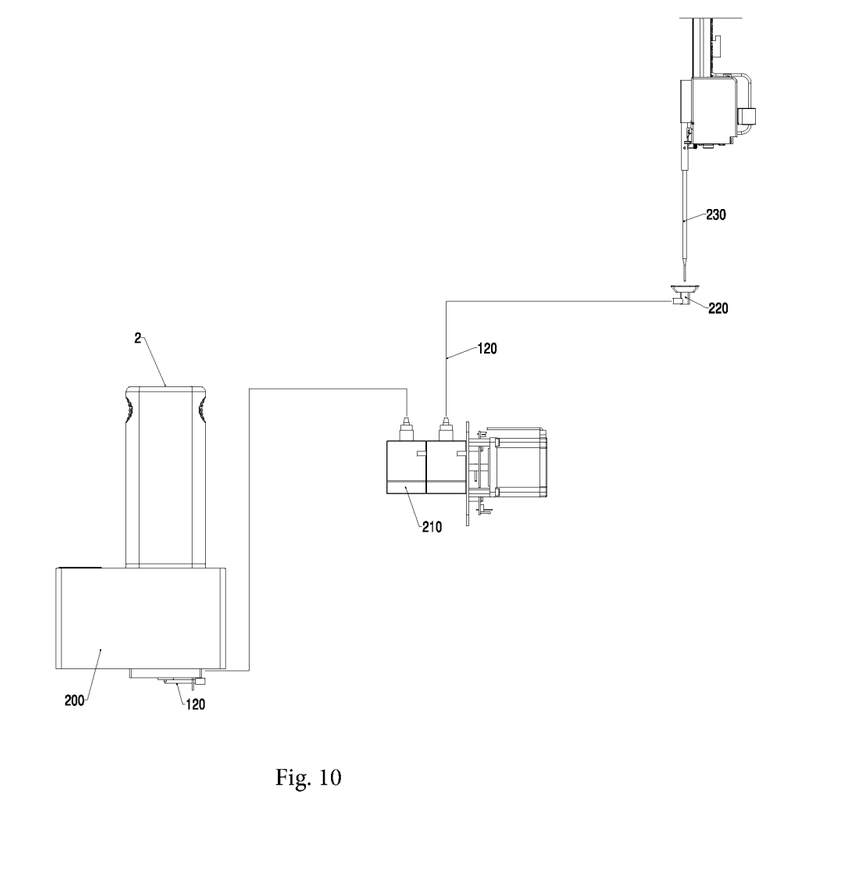
FIG. 10 is a schematic depiction of a docking station connected to a reservoir for providing reagents to a pipettor.

FIG. 10 shows a schematic depiction of a docking station 200 with container 2 being connected via tubing 120 to pumps 210. The pumps are connected by tubing 120 to a reservoir 220 that provides liquids coming from docking station 200 to other modules like a pipettor 230.

Figure 11:
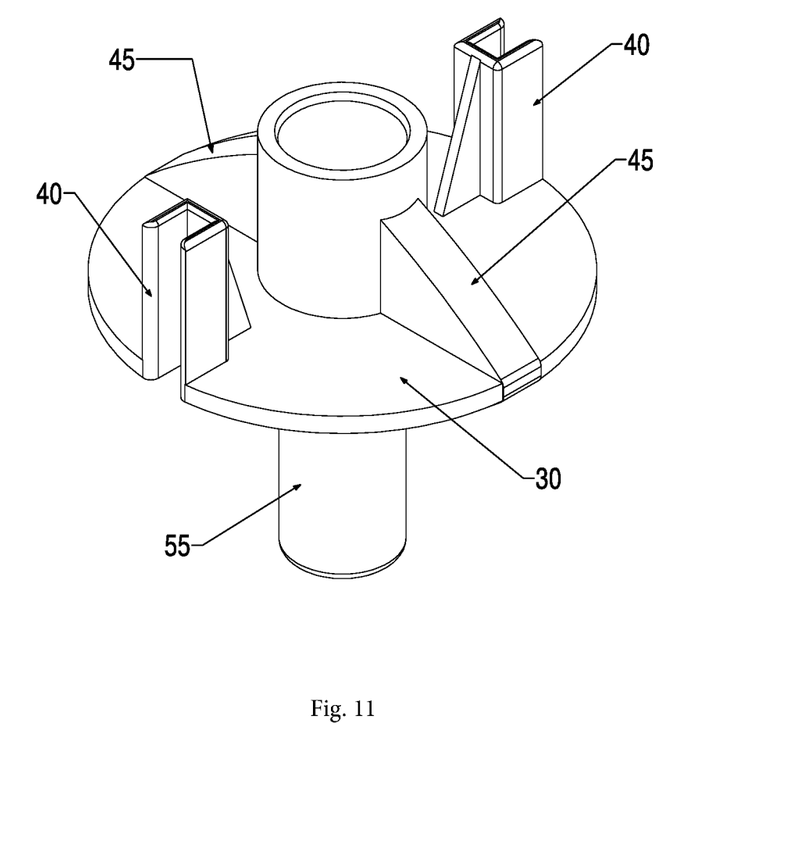
FIG. 11 shows another embodiment of a valve in accordance with the present invention.

FIG. 11 shows another embodiment of a valve according to the instant disclosure. Disk 30 surrounds tube 55. The connectors 45 are arranged perpendicular to disk 30. Valve stops 40 are arranged at the side of disk 30 that is directed to the bottle. Valve stops 40 have the form of a u-profile, which will accommodate into a recess of collar 15 (not shown). The advantage of the embodiment of FIG. 11 is that the arrangement of valve stops 40 in a recess of collar 15 prevents rotation of the valve within the collar.

Figure 12:
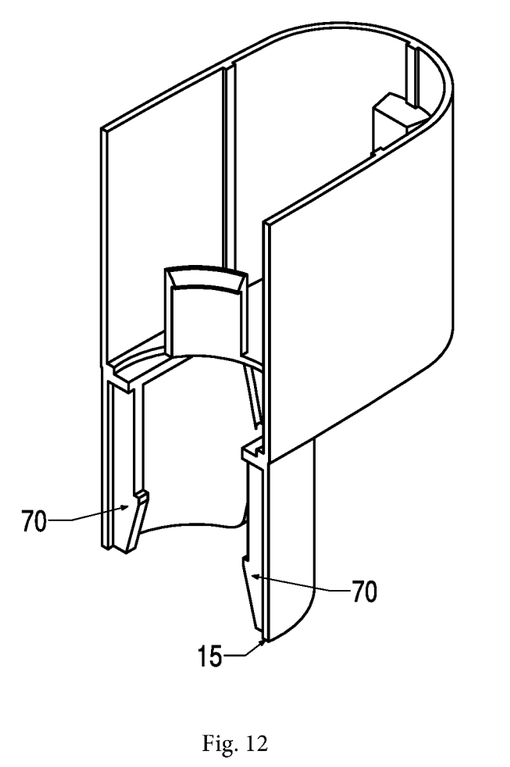
FIG. 12 shows a sectional view of cap 10 in the valve shown in FIG. 11.

FIG. 12 shows a sectional view of cap 10. Collar valve stops 70 for valve stops 40 of the valve shown are depicted. The section of FIG. 12 goes directly through the recess in collar 15 for accommodating the valve stops 40. It can be seen that collar valve stops 70 have projections which will prevent disk 30 (not shown) from moving further.

Figure 13:
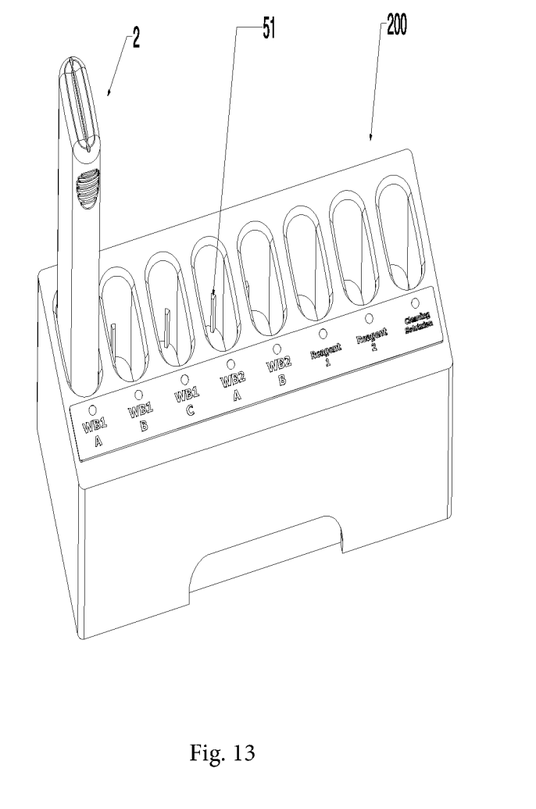
FIG. 13 is a perspective view of an alternative embodiment of a docking station in accordance with a preferred embodiment of the present invention.

FIG. 13 shows a partially loaded docking station having ridge element 51 for engaging with key 50 in the cap.

REFERENCE NUMERALS 1 rigid outer shell
2 container 3 opening of container
5 valve
10 cap
15 collar
20 collar openings
21 division bars
25 RFID tag
30 disk
35 filter
40 valve stop
41 bottom part of snap-fit
45 connector
50 groove or key
51 ridge
55 tube
60 spout
65 plug
70 collar valve stop
75 gasket
100 lever
110 socket
111 opening of socket
120 tubing
125 spring
130 socket gasket
140 magnet
141 sensor
200 docking station
210 pumps
220 reservoir
230 pipettor

What is claimed is:

1. A system for connecting a reagent container to a socket comprising:
 a reagent container for storing and providing liquids, wherein the container has a cap with an outlet comprising a collar having at least one opening on its side, the collar surrounding a spout with a movable valve; wherein the valve comprises a tube that is surrounded by a disk and a plug is centrally arranged within one end of the tube so that the outer walls of the spout form-fit with the inner side of the valve's tube and the inner walls of the spout form-fit with the outer side of the plug for closing the spout, wherein the plug is connected to the one end of the tube; and
 a socket for accommodating the outlet of the container's cap, wherein the socket comprises at least two movable levers to engage into the openings of the collar and a socket gasket for taking up the tube of the valve on one side and tubing on the opposite side to drain the liquids.

2. The system of claim 1, wherein the movable levers of the socket are spring loaded.

3. The system of claim 1, wherein the disk of the valve is centrally arranged in at least one conically shaped connector tapering off starting at the tube of the valve.

4. The system of claim 1, wherein the spout of the cap comprises a filter.

5. The system of claim 1, wherein the outlet of the container and the socket form-fit.

6. The system of claim 1, wherein the valve and the collar have means to limit maximal movement of the valve during opening.

7. The system of claim 1, further comprising a docking station having a tongue suitable to engage in a corresponding groove of the cap to ensure insertion of correct container.

8. The system claim 1, wherein at least two sockets are arranged in a docking station.

9. The system of claim 1, wherein the container is a bottle with a rigid outer shell and a flexible inner bag.

10. The system of claim 9, wherein the outer shell has at least one opening for pressure compensation.

11. The system of claim 9, wherein outer shell and inner bag are made of an opaque material.

12. The system of claim 1, wherein the cap comprises a tag for storing information regarding the content or intended use of content of the container.

13. The system of claim 12, wherein the tag is a RFID label or a barcode.

* * * * *